(12) United States Patent
Ross et al.

(10) Patent No.: US 6,264,659 B1
(45) Date of Patent: Jul. 24, 2001

(54) METHOD OF TREATING AN INTERVERTEBRAL DISK

(76) Inventors: Anthony C. Ross, 4928 Pointe Pleasant La., Hollywood, SC (US) 29449; Peter A. Guagliano, 370 Bay Ridge Pkwy., Brooklyn, NY (US) 11209

( * ) Notice: Subject to any disclaimer, the term of this patent is extended or adjusted under 35 U.S.C. 154(b) by 0 days.

(21) Appl. No.: 09/456,375

(22) Filed: Dec. 8, 1999

Related U.S. Application Data

(63) Continuation-in-part of application No. 09/274,217, filed on Mar. 23, 1999, now Pat. No. 6,183,518, which is a continuation-in-part of application No. 09/255,372, filed on Feb. 22, 1999.

(51) Int. Cl.[7] .................................................. A61B 17/56
(52) U.S. Cl. ............................................ 606/93; 623/23.62
(58) Field of Search ................................ 606/92, 93, 94; 623/17.16, 17.11, 23.62, 23.61

(56) References Cited

U.S. PATENT DOCUMENTS

| 5,047,055 | 9/1991 | Bao et al. ............................ 623/17 |
|---|---|---|
| 5,431,654 | * 7/1995 | Nic ........................................ 606/93 |
| 5,462,542 | * 10/1995 | Kiester ................................. 606/92 |
| 5,545,229 | 8/1996 | Parsons et al. . |
| 5,800,549 | 9/1998 | Bao et al. . |
| 5,925,051 | * 7/1999 | Mikhail ............................... 606/93 |
| 6,183,518 | * 2/2001 | Ross et al. ........................... 606/17 |

* cited by examiner

Primary Examiner—Paul J. Hirsch
(74) Attorney, Agent, or Firm—Browning Bushman

(57) ABSTRACT

A process of injecting a thermoplastic material (20) within an annulus fibrosus of a selected intervertebral disk. The thermoplastic material (20) is heated by an injection device to a predetermined high temperature to provide flow of the thermoplastic material from a needle into the annulus fibrosus of the disk upon injection. After injection, the thermoplastic material is cooled by the body temperature of the patient for setting of the thermoplastic material in a non-flowing state while retaining a suitable resilience to provide desired cushioning. The thermoplastic material (20) may also be injected into an abnormal curvature of the spine to correct the abnormal curvature. The preferred thermoplastic material is gutta percha or a gutta percha compound.

22 Claims, 4 Drawing Sheets

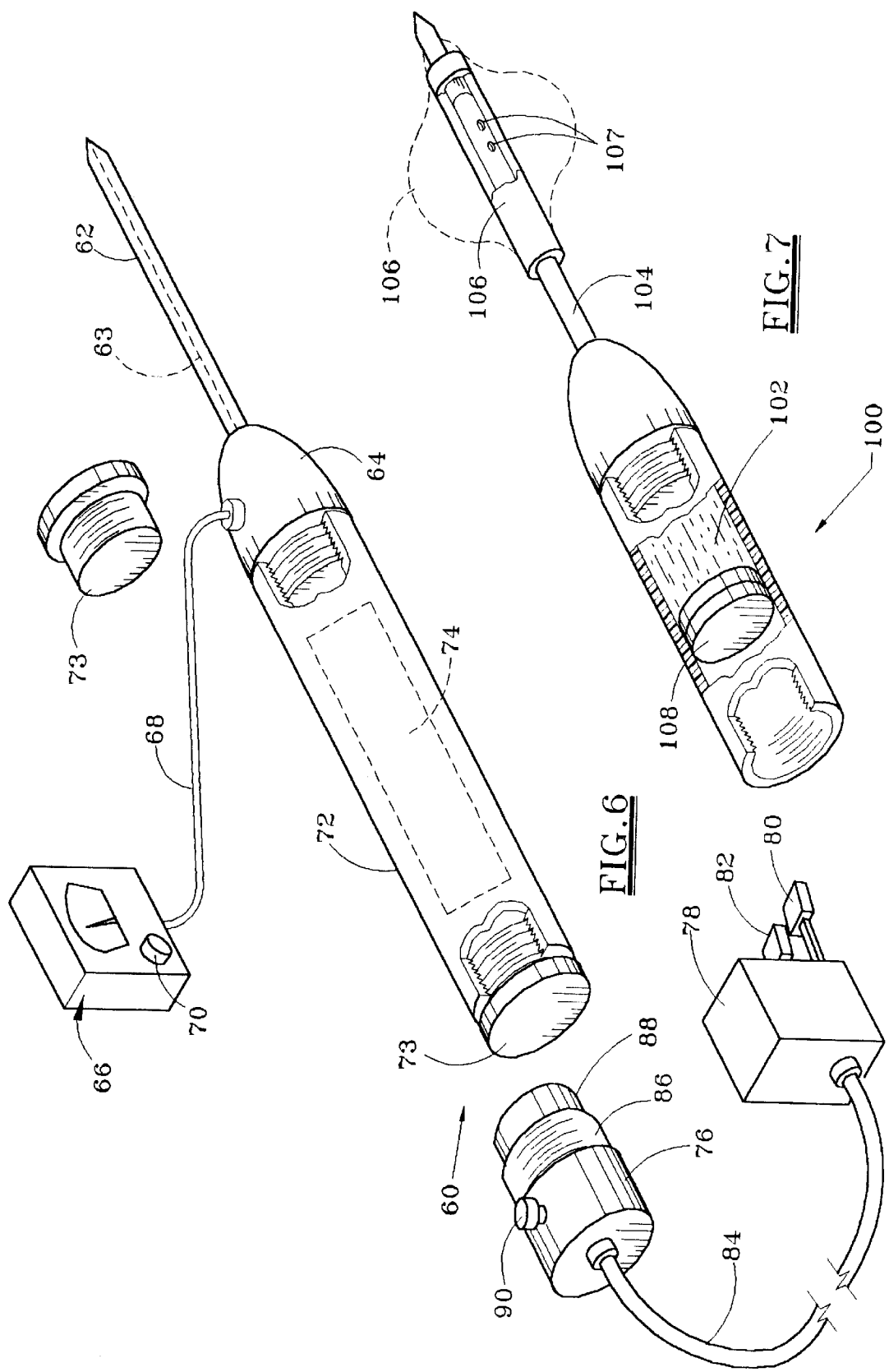

METHOD OF TREATING AN INTERVERTEBRAL DISK

CROSS REFERENCE TO RELATED APPLICATIONS

This is a continuation-in-part of application Ser. No. 09/274,217 filed Mar. 23, 1999 U.S. Pat. No. 6,183,518; which is a continuation-in-part of application Ser. No. 09/255,372, filed Feb. 22, 1999 pending.

FIELD OF THE INVENTION

This invention relates to surgical methods generally, and is more specifically related to a process of treating the intervertebral disk of mammals.

BACKGROUND OF THE INVENTION

The intervertebral disk is a disk with fibrous bands occupying the space between two vertebrae. The anatomy of the disk provides a cushion to allow motion, limit motion and provide space, distancing the vertebra off the nerves and compressible tissue. Part of the vertebrae are bony blocks, which, when stacked one upon the other, form the anterior portion of the spine. The fibrosus band includes an outer annulus fibrosus which surrounds an inner nucleus pulposus. Annulus fibrosus, as referred to herein, is the marginal or peripheral portion of an intervertebral disk. Intervertebral disks are prone to injury. Due to the low blood supply to this area, intervertebral disks are slow to heal, and may not materially heal. When the annulus fibrosus is torn, or punctured, the nucleus pulposus can leak or migrate from the annulus fibrosus. The nucleus pulposus is a substance of jelly like consistency found in the center of an intervertebral disk and flows from the associated annulus fibrosus when the annulus fibrosus is ruptured or prolapsed.

The effect of a ruptured or prolapsed annulus fibrosus may result in spasm, and neurological compromise, such as the compressed nerve and other compressible soft tissues, i.e. arteries, veins. Degeneration of the condition may increase overtime, resulting in chronic and debilitating pain. The condition is usually disabling.

Suppressive measures include steroidal injection, removal of the nucleus pulposus, and fusion either by donor bone, coral or by metal bracing. If disk removal is performed, a healthy part of the disk is often taken, eradicating the function of the joint, and accelerating the degeneration of adjacent segments of the body, as the body attempts to stabilize. This approach frequently leaves the patient immunologically and structurally compromised if not permanently disabled.

Isolated treatment to only the damaged structures employing the most non-invasive procedure possible is preferred. This approach allows as much of the healthy tissue as possible to remain, and to retain normal neurological function. While the offending material can be removed, the material must be replaced with a material which will perform the function formerly performed by the material removed. A need exists for a process which limits the material removed from the intervertebral disk, and which replaces the material so removed with a composition that is physiologically acceptable to the human body, and which allows the intervertebral disk to retain motion and characteristics of normal joint function, including cushioning the joint as compression is introduced from the stacking of the vertebrae. The thermoplastic material must be pliable in its application, and non-flowing after replacement.

In addition, many patients suffer from scoliosis or lateral curvature of the spine. The most common remedy at the present time is the fusion normally by donor bone or metal bracing which oftentimes is not successful or only partially successful. Pain normally accompanies scoliosis and pain suppressants may result in an undesirable chemical dependency in some instances. A need exists to correct the abnormal curvature of the spine without utilizing fusion techniques applied to the spine.

SUMMARY OF THE INVENTION

The present invention is particularly directed to a process for treating the spine including the injection of a thermoplastic material heated to a predetermined temperature for injection into the nucleus pulposus in a flowing state where it cools and sets at body temperature into a non-flowing state. A thermoplastic or thermoplastic polymer material is any plastic or organic material that softens when heated and hardens when cooled. The thermoplastic material prior to injection is heated to a temperature sufficient for the material to flow under pressure into the nucleus pulposus and, after it sets into a non-flowing state at body temperature, the material retains sufficient resilience to provide desired cushioning of the spine.

A thermoplastic material which has been found to be highly satisfactory is gutta percha which is normally combined with other elements or ingredients in a suitable gutta percha compound. Gutta percha is a linear crystalline polymer which melts at a predetermined temperature a random but distinct change in structure results. Normal body temperature is 37 C. and a suitable thermoplastic material hardens into a non-flowing state at a temperature range between about 35 C. and 42 C. (the degree symbol for temperature is omitted in all references herein to a specific temperature). A crystalline phase appears in two forms; an alpha phase and a beta phase. The alpha form is the material that comes from the natural tree product. The processed form is the beta form. When heated, gutta percha undergoes phase transitions. When there is a temperature increase, there is a transition from beta phase to alpha phase at about 46 C. The gutta percha changes to an amorphous phase about 54 C. to 60 C. When cooled very slowly, about 1 C. per hour, the gutta percha crystallizes to the alpha phase. Normal cooling returns the gutta percha to the beta phase. Gutta percha softens at a temperature above about 64 C. A suitable gutta percha compound is dental gutta percha which contains by weight only about 20% gutta percha with zinc oxide comprising about 60% to 75% of the material. The remaining 5% to 10% consists of various resins, waxes, and metal sulfates. The percentages listed are directed to an optimum gutta percha compound. The preferred percentage of gutta percha is in the range of 15% to 40%. Zinc oxide and metals in the gutta percha compound are desirable for imaging such as X-rays while resins and waxes are desirable for obtaining an adequate flow of the thermoplastic material. Gutta percha provides the desired resiliency at body temperature and is at least about 15% of the compound. Zinc oxide also provides an anti-inflammatory property. In some instances, a mineral trioxide aggregate may be added to the gutta percha compound.

An injection device, such as an injection gun, is utilized for heating and injecting the thermoplastic material under a predetermined pressure within the spine. The injection device may utilize a silver needle, encased in ceramics, of about 20 to 30 centimeters in length with a diameter as high as 1 centimeter. The size of the needle may depend on such factors as the amount of thermoplastic material to be injected, the temperature of the thermoplastic being injected, and the axial pressure applied by the injection device, such as a piston or plunger, to the thermoplastic material to force the heated material from the end of the needle into the spine. The thermoplastic material is physiologically acceptable to the human body.

When the thermoplastic material is utilized to treat a ruptured annulus fibrosus, the nucleus pulposus is removed and the material removed is replaced by the heated thermoplastic material which sets at body temperature and provides sufficient resilience after setting to permit adequate motion and cushioning of the vertebrae. The cushioning effect of the gutta percha compound provides a semimobile disk as a buffer to a fusion to reduce the possibility of sequential iatrogenic disk degeneration. The thermoplastic material is injected within the annulus fibrosus to replace the removed nucleus pulposus by a needle of the injection device.

When the thermoplastic material is injected within the spine to reduce a scoliosis, the material is sequentially injected by a needle of the injection device into the annulus fibrosus or interannular at the apex and adjacent joints of the concavity of the scoliosis. Such an injection tends to straighten the curvature of the spine is a wedge-like action.

It is an object of the present invention to provide a process of injecting a thermoplastic material into the annulus fibrosus of a spine.

A further object of the present invention is to provide such a process in which the thermoplastic material is heated to a predetermined temperature for flow into the annulus fibrosus and hardens when it cools from body temperature into a non-flowing state to form a resilient support for cushioning between vertebrae.

Another object of the invention is to provide a process to treat a ruptured annulus fibrosus of a spine by removal of the nucleus pulposus and injection of a thermoplastic material into the annulus fibrosus to replace the nucleus pulposus.

Other objects, features, and advantages of the invention will be apparent from the following specification and drawings.

BRIEF DESCRIPTION OF THE DRAWINGS

FIG. 6 is a perspective view of a modified injecting device for injecting a thermoplastic material within the spine; and FIG. 7 is a perspective view of a disk dilator.

DETAILED DESCRIPTION OF THE PREFERRED EMBODIMENTS

Figure 1:
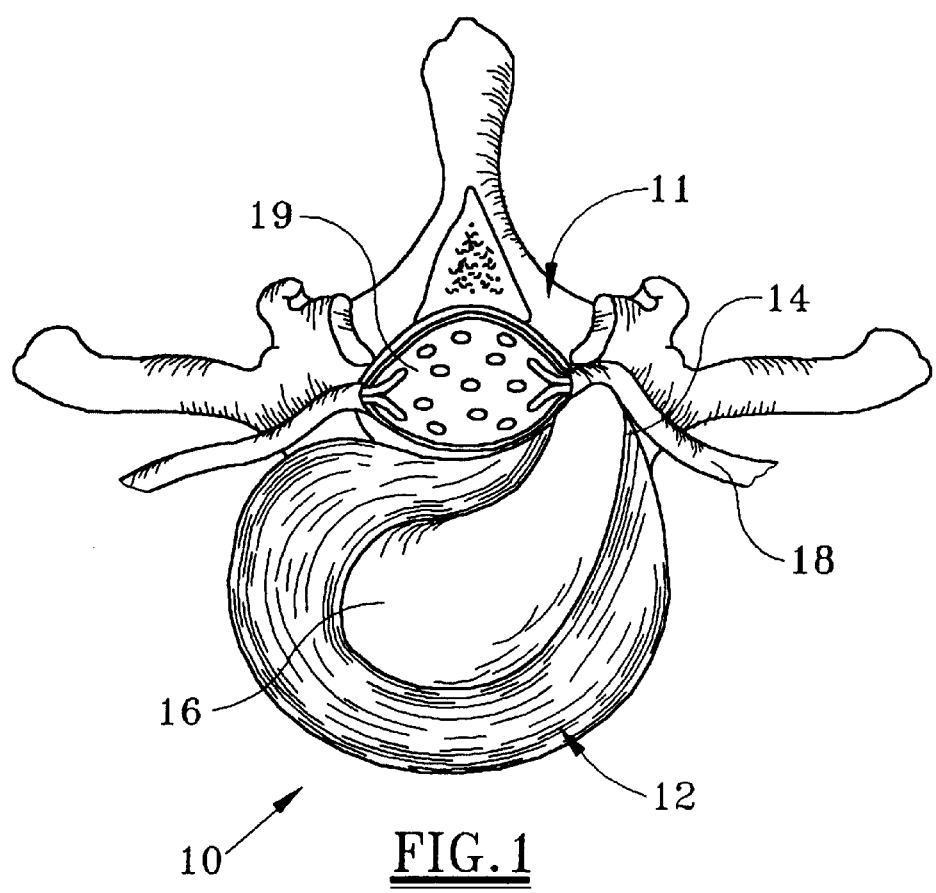
FIG. 1 is a diagrammatic view of a ruptured/prolapsed annulus fibrosus and the resulting migrated nucleus pulposus of an intervertebral disk.
Figure 2:
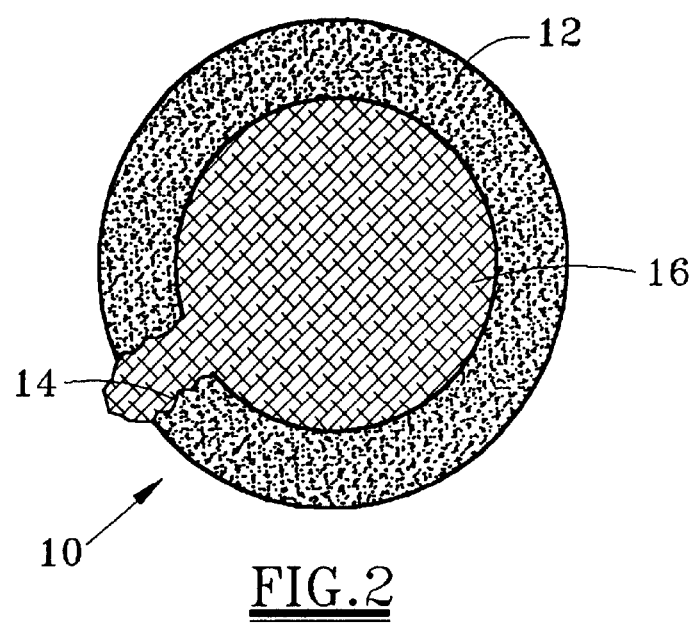
FIG. 2 is a sectional view of the ruptured annulus fibrosus showing leakage of the nucleus pulposus.

Referring now to the drawings for a better understanding of the invention, and more particularly to the embodiment shown in FIGS. 1–4, a portion of a spine is shown generally pictorially in FIG. 1 including an intervertebral disk 10 adjacent a vertebra 11. Disk 10 has an annulus fibrosus 12 which has ruptured at 14 resulting in a leakage or migration of nucleus pulposus 16 from the annulus fibrosus 12. A sacral nerve is shown at 18 extending from the cauda eqina 19 and the migrating or flowing nucleus pulposus 16 may result in a compression of nerve 18.

It is desired to remove nucleus pulposus 16 which flows at body temperature and replace it with a thermoplastic material which does not flow at body temperature (37 C.). FIGS. 1–4 illustrate the removal of the nucleus pulposus 16 and replacement with a thermoplastic material. For this purpose the rupture or prolapse of the annulus fibrosus 12 is first identified and isolated. This identification and isolation is by means such as X-ray, MRI or other diagnostic imaging procedures which are diagnostically acceptable. After the area of rupture or prolapse is identified and isolated the site is surgically accessed. Since it is a goal of the invention to minimize trauma associated with the procedure, it is preferred to access the site through an arthroscopic procedure, or technology that involves minimal invasion and offense to healthy areas of the annulus fibrosus 12, while damaged parts of the intervertebral disk are removed. Current technology allows for surgical removal of nucleus pulposus 16 by irrigation and suction.

The nucleus pulposus 16 removed is replaced with a thermoplastic material which is physiologically acceptable to the human body and flows when injected but hardens at body temperature into a non-flowing resilient material. The thermoplastic material is first heated by a suitable injection device having an injection needle to a predetermined temperature for flow under pressure from the needle into the annulus fibrosus 12 wherein the nucleus pulposus 16 has been removed. A thermoplastic material which has been found to be highly satisfactory is gutta percha or a gutta percha compound. Gutta percha is a geometric isomer of natural rubber. A substance such as mineral trioxide aggregate and other anti-inflammatory elements may be added to the gutta percha to facilitate the binding properties and to facilitate healing of the affected area. Dental gutta percha which may be utilized contains approximately 20% gutta percha, with zinc oxide comprising 60% to 75% of the material. The remaining 5% to 10% consists of various resins, waxes, metal sulfates for radioopacity, and coloration. When cold, gutta percha is relatively inelastic, but as it warms it becomes moldable. At a high temperature gutta percha will flow under pressure to permit injection from an injection needle into the annulus fibrosus 12.

Figure 3:
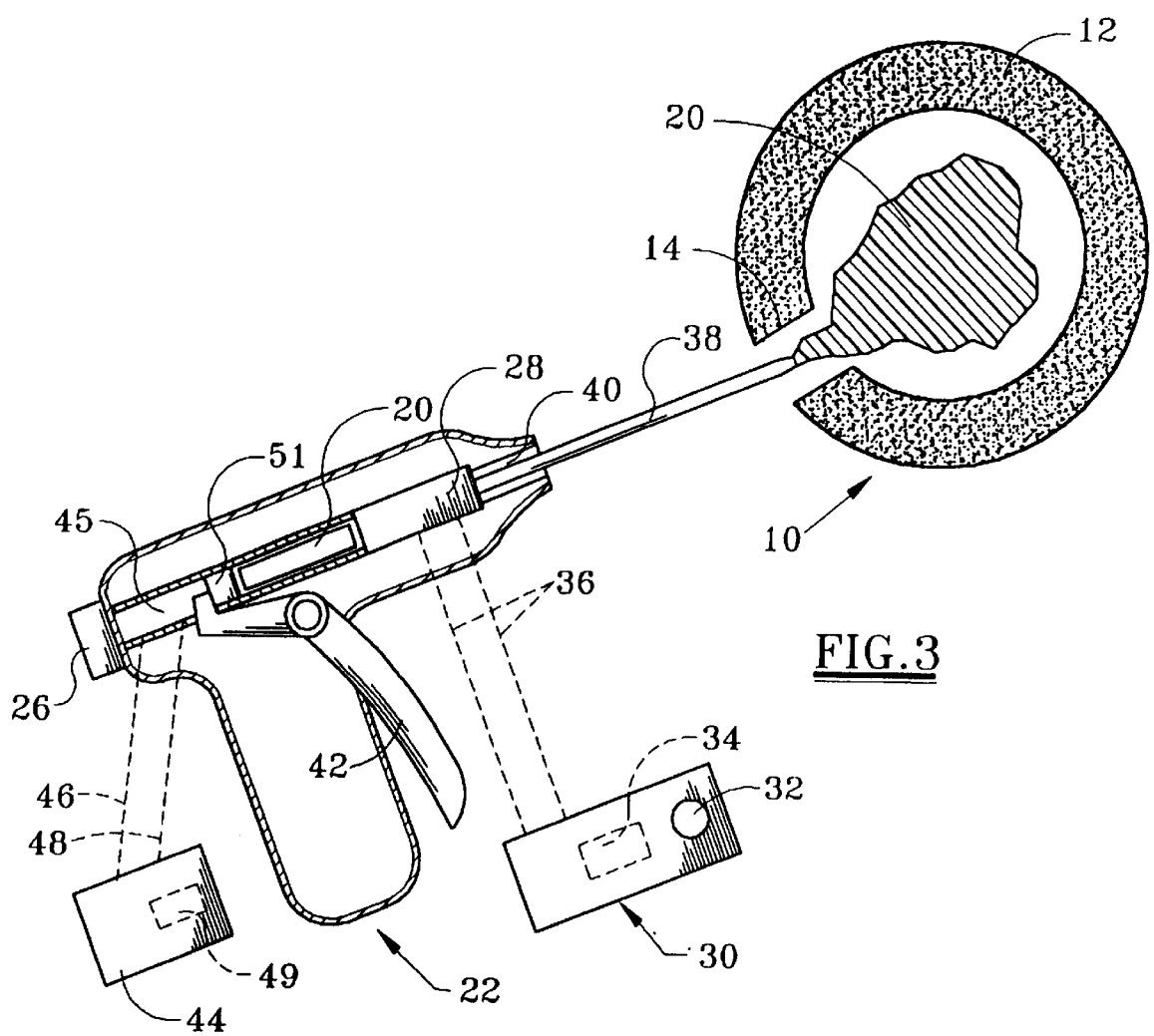
FIG. 3 is a diagrammatic view illustrating injection of a thermoplastic material by an injecting device into the annulus fibrosus for replacement of the nucleus pulposus.
Figure 4:
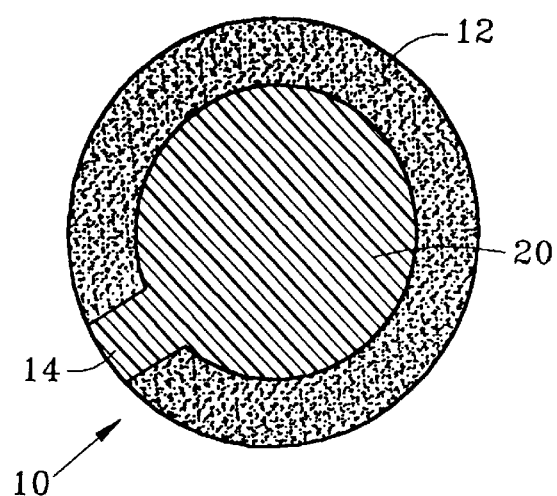
FIG. 4 shows the intervertebral disk after setting of the thermoplastic material.

Referring particularly to FIG. 3, injection of thermoplastic material 20 within the annulus fibrosus 12 by an injection device or gun illustrated schematically at 22 is shown. Injection gun 22 has a body 24 with a removable plunger 26 adapted to receive a cylindrical plug of the thermoplastic material 20. A heater 28 is provided to heat the thermoplastic material 20 and a heater control unit 30 having an adjustable temperature control knob 32 is provided with a temperature readout at 34. Electrical leads 36 extend to heater 28. An injection needle 38 preferably formed of silver extends from body 24 and has a ceramic sheath 40 about a portion of needle 38. A hand operated trigger 42 may be activated for forcing thermoplastic material 20 from the end of needle 38 upon heating of the thermoplastic material 20 to a predetermined temperature. To assist trigger 42 in exerting an axial force against the plug of thermoplastic material 20 in gun 22, a foot operated hydraulic pump may be provided at 44 to supply fluid through lines 46, 48 to a hydraulic cylinder 45. A pressure readout is provided at 49. A suitable piston 51 may exert an axial force against the thermoplastic material 20. A hydraulic system is effective in providing an axial injection force that may be easily regulated and controlled by personnel performing the procedure. A suitable injection device designated as a Obtura II Heated Gutta Percha System may be purchased from Obtura of Fenton, Mo.

Needle 38 preferably formed of silver may be of various diameters but will not exceed a diameter of about 1 centimeter. Needle 38 may have a length of between 20 centimeters and 30 centimeters. A plug or stick of the thermoplastic material 20 may have a total volume of about 21 cubic centimeters with a diameter of about 16 millimeters and a length of about 10½ centimeters. The thermoplastic material 20 is required to be heated prior to injection to permit flow of the thermoplastic material. The higher the temperature of the thermoplastic material, the lower the viscosity and the faster flow. A lower temperature heating increases the viscosity and retards the flow rate. The degree to which the thermoplastic material 20 is heated may vary substantially dependent primarily on the diameter of needle 38 and the axial force applied to the heated thermoplastic material for injection. Generally the lowest temperature to which the thermoplastic material is heated while utilizing a large diameter needle such as 1 centimeter in diameter with a relatively high axial force may be 50 C. while the highest temperature will be less than about 250 C. The optimum temperature is about 185 C. within an optimum range between about 150 C. and 200 C.

It is desirable for the thermoplastic material to have a viscosity and temperature suitable for injection and flow into the space previously occupied by the annulus fibrosus 12. After injection of the thermoplastic material 20 into the annulus fibrosus 12, the material flows to fill the entire void area of the annulus fibrosus possibly including the ruptured area 14. The thermoplastic material 20 cools relatively rapidly and, for example, reaches body temperature about its outer surface very quickly if injected at a temperature of about 185 C. and then cools internally to body temperature in several minutes depending primarily on the thickness and surface area of the thermoplastic material. The thermoplastic material 20 tends to set at about 42 C. and is not in a flowing state lower than about 42 C. Upon reaching the body temperature of 37 C., the thermoplastic material is set. At normal human body temperature the thermoplastic material is no longer moldable and is not flowing or migrating. Thus, the thermoplastic material 20 remains within the annulus fibrosus 16 and repairs the rupture 14 of the annulus fibrosus. It is, however, necessary that the thermoplastic material retain sufficient resilience in order to provide in a satisfactory manner the functions of allowing motion and adequately cushioning of the joint between associated vertebrae. If necessary, the thermoplastic material 20 may be subsequently removed from the annulus fibrosus 12 by surgical, physical, enzymatic, and/or chemical means.

Figure 5:
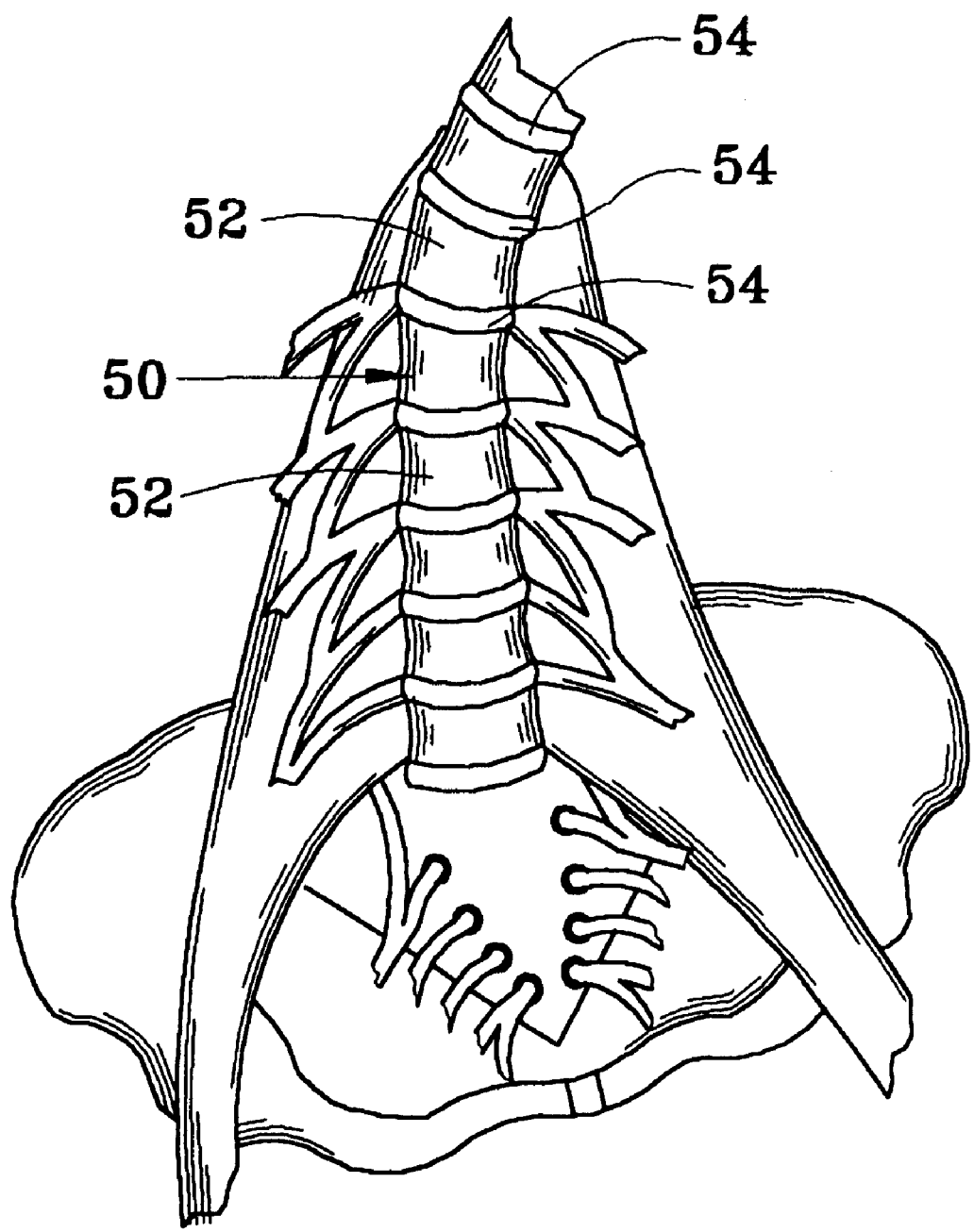
FIG. 5 illustrates the abnormal curvature of the lower spine and the injection of a thermoplastic material into the curved concave portion of the spine.

Referring now to FIG. 5, a spinal column is shown generally at 50 having vertebrae 52 with intervertebral disks 54 positioned therebetween. FIG. 5 shows spine 50 with scoliosis or abnormal curvature of the spine. The abnormal curvature of spine 50 provides a concave curvature as shown in FIG. 5 at which disks 34 are positioned. To correct or remedy the abnormal curvature of spine 50, a thermoplastic material 20 may be injected at intervertebral disks 54 progressively to reduce the concavity for flow into the associated annulus fibrosus as in the procedure set forth in FIGS. 1–4. The amount of the injected material will vary with the greatest amount of injected material at the greatest deflection and the least amount at the disks closest to the terminal ends of the abnormal curvature. However, the nucleus pulposus is not removed from the spine 50. The injected material provides a force acting as a wedge to reduce the concavity of the scoliosis. Gutta percha as set forth in the embodiment of FIGS. 1–4 is the preferred material for the thermoplastic material to be injected.

Referring to FIG. 6, a modified injection device is shown generally at 60 including an injection needle 62, a heater 64 receiving an inner end portion of needle 62, and an electrical heater control element 66 having leads 68 extending to heater 64. A suitable control knob 70 controls the temperature and a readout panel indicates the temperature which, for example, may be about 185 C.

A generally cylindrical chamber or housing 72 adjacent heater 64 is provided to receive a cylindrical plug 74 of the thermoplastic material. Housing 72 has open ends to receive removable threaded end plugs 73 for maintaining plug 74 in a sealed relation. One plug 73 is shown removed from housing 72 in FIG. 6. Plug 74 may also be covered with a suitable cover which may be manually removed for use, either in combination with or without end plugs 73. Housing 72 upon removal of plugs 73 may be connected to heater 64 at one end and connected to a fluid pressure chamber 76 at an opposed end. A suitable fluid from a reservoir 78 having a foot operated pedal 80 and a vent 82 is supplied through line 84 to pressure chamber 76. Concentric pistons 86 and 88 responsive to pressurized fluid in chamber 76 are provided to engage the end of thermoplastic plug 74 to urge plug 74 into heater 64 for injection from needle 62 under a predetermined pressure. A pressure gauge 90 is provided to indicate the fluid pressure applied against thermoplastic plug 74. In some instances, housing 72 may be disposable with heater 64 being of an increased length to receive the entire length of plug 74.

Needle 62 is preferably about 6 mm in diameter, and between about 20 cm and 30 cm in length for maneuverability. The volume of thermoplastic material to purge needle 62 may be between about 5.65 cc and 8.48 cc dependent on the size of the needle. Approximately 15 cc of thermoplastic material may be utilized for injection within the spine. Cylindrical plug 74 may have a total volume of 21 cc with a diameter of 16 mm and a length of 10.45 cm to provide a compact unit.

It may be desirable in some instances to provide a heater tape 63 in needle 62 for heating of the projecting needle 62. Needle 62 may be formed of a ceramic material and preferably includes an inner silver liner for receiving heater tape 63 which may be formed of a suitable material to provide an electrical resistance, for example. Needle 62, heater 64 and housing 72 may comprise separate injection subassemblies removably connected to pressure chamber 76 by a suitable threaded connection thereby to provide disposable units if desired with leads 68 detached from heater 64. The fluid for the hydraulic system for fluid cylinder 76 may be water or another innocuous fluid.

Also shown in FIG. 7 as an attachment is a disk dilator assembly generally indicated at 100 having a cylindrical chamber 102 with an inert fluid such as saline therein and a piston 108 for pressurizing the fluid. Disk dilator assembly 100 is designed for detachable connection to pressure chamber 76 of the injector device of FIG. 6 for the supply of hydraulic fluid for acting against piston 108. A detachable balloon dilator sleeve 106 extends about the extending end of needle 104 having lateral openings 107. Piston 108 is effective to pressurize the fluid for flow through openings 107 for expansion of sleeve 106 as shown in broken lines in FIG. 7. Dilator sleeve 106 upon injection of needle 104 in a disk of the spine is expanded for exerting an expanding force against the disk.

While gutta percha or a gutta percha compound including at least about 15% of the compound by weight is the preferred thermoplastic material, it is understood that other types of thermoplastic material may be suitable if in a non-flowing state at body temperature (37 C.) and in a flowing state when heated over at least about 50 C. for injection from a needle of an injection device. Various other ingredients or elements may be added to the gutta percha compound in various percentages. Further, while specific injection devices have been illustrated for injection of the thermoplastic material, other types of injection devices for heating the thermoplastic material and for applying an axial force against the thermoplastic material for injection may be provided. For example, various devices may be provided for heating the thermoplastic material prior to injection and for pressurizing the thermoplastic material for controlled flow of the thermoplastic material through an injection needle for injection. Thus, while preferred embodiments of the present invention have been illustrated in detail, it is apparent that modifications and adaptations of the preferred embodiments will occur to those skilled in the art. However, it is to be expressly understood that such modifications and adaptations are within the spirit and scope of the present invention as set forth in the following claims.

What is claimed is:

1. A process of replacing nucleus pulposus of an intervertebral disk, comprising:
   identifying a location of a rupture in an annulus fibrosus of an intervertebral disk;
   removing nucleus pulposus associated with said annulus fibrosus of said intervertebral disk; and
   injecting a thermoplastic material heated to a temperature over 50 C. for flowing into said annulus fibrosus and then permitting said material to cool for setting in a non-flowing state upon reaching a temperature of between 35 C. and 42 C., so as to cause said material to occupy a space formerly occupied by said nucleus pulposus.

2. The process as defined in claim 1, further comprising:
   providing an injection device for injecting the thermoplastic material, the injection device having a heating element and a needle for dispensing of the thermoplastic material;
   heating the thermoplastic material by said heating element to a predetermined high temperature over 50 C. at which said material flows a desired amount; and
   thereafter injecting said thermoplastic material at said predetermined high temperature through said needle for flow into said annulus fibrosus of said selected intervertebral disk.

3. The process as defined in claim 1 wherein injecting a thermoplastic material includes injecting gutta percha heated to a temperature over 50 C. for flowing of said gutta percha into said annulus fibrosus.

4. The process as defined in claim 1 wherein injecting a thermoplastic material includes injecting a gutta percha compound including zinc oxide and heated to a temperature between about 150 C. and 200 C.; and
   cooling said gutta percha compound by body temperature to about 37 C. for setting of said gutta percha compound in a non-flowing state with sufficient resilience to provide adequate cushioning.

5. A process of injecting a thermoplastic material within an annulus fibrosus of a selected intervertebral disk of a patient comprising:
   selecting said intervertebral disk in which said thermoplastic material is to be injected;
   providing an injection device for the thermoplastic material having a heating element for the thermoplastic material and a needle for dispensing of the thermoplastic material;
   heating the thermoplastic material by said heating element to a predetermined high temperature at which said material flows a desired amount;
   thereafter injecting said thermoplastic material at said predetermined high temperature through said needle for flow into said annulus fibrosus of said selected intervertebral disk; and
   cooling said thermoplastic material to the body temperature of the patient for setting of said thermoplastic material in a non-flowing state with a resilience to provide desired cushioning.

6. The process as defined in claim 5, further comprising:
   removing nucleus pulposus from said annulus fibrosus prior to injection of said thermoplastic material wherein said thermoplastic material occupies a space formerly occupied by said nucleus pulposus.

7. The process as defined in claim 5 wherein:
   selecting said intervertebral disk includes selecting an intervertebral disk at the apex of a abnormal curvature of the spine of the patient; and
   then injecting said thermoplastic material at said predetermined high temperature into the annulus fibrosus of said selected disk.

8. The process as defined in claim 5 wherein:
   injecting a thermoplastic material includes injecting gutta percha heated to a temperature over 50 C.

9. The process as defined in claim 5 wherein:
   Injecting a thermoplastic material includes injecting gutta percha heated for flowing at a temperature between about 150 C. and 200 C.; and
   cooling said gutta percha by body temperature at about 37 C. for setting in a non-flowing state.

10. A process for treating scoliosis of the spine at the greatest deflection of the concavity of the spine formed by the abnormal curvature comprising:
    selecting an intervertebral disk at the apex of the concavity:
    injecting a thermoplastic material heated to a temperature over 50 C. for flowing into the annulus fibrosus of said intervertebral disk; and
    permitting said thermoplastic material to cool to body temperature of a patient for setting in a non-flowing state while retaining sufficient resilience for cushioning and non-migration.

11. The process as defined in claim 10, further comprising:
    providing an injection device for injecting the thermoplastic material, the injection device having a heating element and a needle for dispensing of the thermoplastic material;
    heating the thermoplastic material by said heating element to a predetermined high temperature over 50 C. at which said material flows a desired amount; and
    thereafter injecting said thermoplastic material at said predetermined high temperature through said needle for flow into said annulus fibrosus of said selected intervertebral disk.

12. The injection device as defined in claim 4, wherein the thermoplastic material comprises a geometric isomer of natural rubber.

13. The injection device as defined in claim 4, wherein said heater heats said thermoplastic material for flowing at a temperature between about 150C and 200C.

14. The injection device as defined in claim 4, wherein said thermoplastic material comprises a linear crystalline polymer.

15. The injection device as defined in claim 4, wherein said thermoplastic material comprises a gutta percha compound in which gutta percha is between 15% and 40% by weight of the compound.

16. The injection device as defined in claim 4, wherein said injection needle is formed of a ceramic material.

17. The injection device as defined in claim 4, further comprising:
    an expandable sleeve about said needle adjacent an extending end of said needle to define an annulus between said needle and said sleeve, so that pressurized fluid communicating with the annulus expands said sleeve outwardly.

18. The injection device as defined in claim 17, wherein said needle has openings thereon for the supply of a pressurized fluid to said annulus for expanding said sleeve.

19. The injection device as defined in claim 4, further comprising:
    a piston adjacent an end of said plug for exerting a force against said plug; and
    a hand operated trigger is operatively connected to said piston and upon actuation is effective to force said thermoplastic material from said needle when said thermoplastic material is heated to a flowing state.

20. The injection device as defined in claim 4, further comprising;
    a hand operated trigger operatively connected to said plug thermoplastic material and upon actuation is effective to force said thermoplastic material from said needle when said thermoplastic material is heated to a flowing state.

21. The injection device as defined in claim 4, further comprising;
    the chamber for receiving the plug is provided in a plunger removable from an injection device body.

22. The injection device asa defined in claim 4, further comprising;
    a heater control unit having an adjustable temperature control to provide a selected temperature for said heater.

* * * * *

UNITED STATES PATENT AND TRADEMARK OFFICE
CERTIFICATE OF CORRECTION

PATENT NO. : 6,264,659 B1
DATED : July 24, 2001
INVENTOR(S) : Ross et al.

Page 1 of 1

It is certified that error appears in the above-identified patent and that said Letters Patent is hereby corrected as shown below:

<u>Column 10,</u>
Line 10, change "thermoplastic material and" to -- of thermoplastic material and --

Signed and Sealed this

Nineteenth Day of March, 2002

Attest:

JAMES E. ROGAN
*Director of the United States Patent and Trademark Office*

*Attesting Officer*